United States Patent
Bourne (10) Patent No.: US 11,400,178 B2
(45) Date of Patent: Aug. 2, 2022

(54) HOLLOW VOLATILE SUBSTANCE DIFFUSER

(71) Applicant: Energizer Brands II, LLC, St. Louis, MO (US)

(72) Inventor: Christopher A. Bourne, Painesville, OH (US)

(73) Assignee: Energizer Group Limited, St. Louis, MO (US)

( * ) Notice: Subject to any disclaimer, the term of this patent is extended or adjusted under 35 U.S.C. 154(b) by 111 days.

(21) Appl. No.: 16/388,407

(22) Filed: Apr. 18, 2019

(65) Prior Publication Data

US 2020/0331326 A1  Oct. 22, 2020

(51) Int. Cl.
*A61L 9/12* (2006.01)
*B60H 3/00* (2006.01)

(52) U.S. Cl.
CPC ............. *A61L 9/12* (2013.01); *A61L 2209/15* (2013.01); *B60H 3/0028* (2013.01)

(58) Field of Classification Search
CPC ..... A61L 9/12; A61L 2209/15; A61L 2209/16
USPC ...................................... 239/34–60
See application file for complete search history.

(56) References Cited

U.S. PATENT DOCUMENTS

| | | |
|---|---|---|
| 2,545,160 A | 3/1951 | Miller |
| 2,547,688 A * | 4/1951 | Brody ................ A01M 1/2055 239/57 |
| 2,673,120 A | 3/1954 | Bink et al. |
| 3,908,905 A | 9/1975 | Von Philipp et al. |
| 4,493,011 A * | 1/1985 | Spector .................... A61L 9/02 239/56 |
| 4,523,717 A | 6/1985 | Schwab |
| 4,903,584 A | 2/1990 | Styles |
| 5,762,549 A | 6/1998 | Scheuer et al. |
| 5,865,372 A | 2/1999 | Ceresko |
| D437,041 S | 1/2001 | Eisenbraun |
| 6,197,263 B1 | 3/2001 | Blount |
| 6,764,656 B1 | 7/2004 | Matulevich |
| 7,246,732 B1 | 7/2007 | Ha |
| D594,954 S | 6/2009 | Wheatley |
| 7,687,037 B2 | 3/2010 | Wheatley et al. |
| 7,687,038 B2 | 3/2010 | Wheatley et al. |
| D640,359 S | 6/2011 | Irvin |
| D650,892 S | 12/2011 | Wheatley et al. |

(Continued)

OTHER PUBLICATIONS

United States Patent and Trademark Office, Office Action for U.S. Appl. No. 15/255,537, dated Mar. 14, 2018, USA.

(Continued)

*Primary Examiner* — Jason J Boeckmann
(74) *Attorney, Agent, or Firm* — Lee & Hayes, P.C.

(57) ABSTRACT

An example embodiment of a volatile substance diffuser comprises a housing defining a housing axis; and a component carrying a volatile substance. The component defines an air passageway there through. The component is secured to an inner surface of the housing. The air passageway defines an air passageway axis and the housing axis and the air passageway axis are approximately parallel. In an example embodiment, the volatile substance diffuser further comprises a clip secured to the housing and configured to removably secure the volatile substance diffuser to a slat of an air vent (e.g., an automobile air vent, building air vent, and/or the like).

20 Claims, 12 Drawing Sheets

(56) References Cited

U.S. PATENT DOCUMENTS

| | | | |
|---|---|---|---|
| 8,147,761 B2 | 4/2012 | Wheatley et al. | |
| 8,215,511 B1 * | 7/2012 | Lin | B65D 39/08 |
| | | | 220/212.5 |
| D667,100 S | 9/2012 | Hakim | |
| D674,071 S | 1/2013 | Browder | |
| 8,460,609 B1 | 6/2013 | Wheatley et al. | |
| 8,480,960 B2 | 7/2013 | Wheatley et al. | |
| D689,181 S | 9/2013 | Irvin et al. | |
| 8,685,330 B2 | 4/2014 | Irvin et al. | |
| 8,978,998 B1 | 3/2015 | Talley | |
| 9,155,812 B1 | 10/2015 | Bourne | |
| 9,314,543 B2 | 4/2016 | Bourne | |
| 10,864,293 B2 * | 12/2020 | Griffis | B65D 51/245 |
| 2004/0000596 A1 * | 1/2004 | Cuthbert | A61L 9/12 |
| | | | 239/34 |
| 2006/0071092 A1 | 4/2006 | Harris, Jr. | |
| 2007/0119963 A1 | 3/2007 | DiBello et al. | |
| 2008/0093474 A1 | 4/2008 | Suissa et al. | |
| 2008/0217426 A1 | 9/2008 | Brown et al. | |
| 2009/0072045 A1 * | 3/2009 | Wheatley | A61L 9/12 |
| | | | 239/56 |
| 2011/0108632 A1 | 5/2011 | Brandenburg et al. | |
| 2013/0341424 A1 | 12/2013 | Brandenburg et al. | |
| 2014/0113538 A1 | 4/2014 | Irvin et al. | |
| 2014/0145004 A1 | 5/2014 | Westphal | |
| 2014/0367484 A1 | 12/2014 | Kramer | |
| 2015/0366250 A1 * | 12/2015 | Landau | A23L 27/88 |
| | | | 426/2 |
| 2016/0166722 A1 | 6/2016 | Mudrick | |

OTHER PUBLICATIONS

United States Patent and Trademark Office, Notice of Allowance for U.S. Appl. No. 15/255,537, dated Sep. 5, 2018, USA.

*Car Air Freshener Auto Outlet Perfume Vent Air Freshener in the Car Air Conditioning Clip Magnet Diffuser Solid Perfume*, [online], [retrieved from the Internet May 7, 2019] <URL: https://sale.aliexpress.com/country@US/_pc/20190506_Fashion_Festival_MOM_TOYS.htm?spm=2114.10010108.100003.1.1ad02d07NRJWQB&gps-id=5209001&scm=1007.15875.101669.0&scm_id=1007.15875.101669.0&scm-url=1007.15875.101669.0&pvid=71e633fe-991c-4209-99e2-4fblec433b76> (6 pages).

*Car Styling Emergency Hammer Style Air Outlet Perfume Freshener Safety Hammer Auto Car Perfumes Clips Air Fresheners for All Car*, [online], [retrieved from the Internet May 7, 2019] <URL: https://www.aliexpress.com/item/Car-Styling-Emergency-Hammer-Style-Air-Outlet-Perfume-Freshener-Safety-Hammer-Auto-Car-Perfume-Clips-Air/32708595157.html> (5 pages).

*Vent Air Freshener & Purifier*, [online], [retrieved from the Internet May 7, 2019] <URL: https://www.gadgetmycar.com/products/car-vent-air-freshener-purifier>, (4 pages).

*Hot RodTM Vent Stick*, [online], [retrieved from the Internet May 7, 2019] <URL: https://handstandspromo.com/products/hot-rod> (7 pages).

* cited by examiner

HOLLOW VOLATILE SUBSTANCE DIFFUSER

TECHNICAL FIELD

Embodiments relate generally to volatile substance diffusers. For example, such as, a hollow air freshener.

BACKGROUND

Various volatile substance diffusers have been proposed, particularly air fresheners for use in vehicles. However, a variety of these volatile substance diffusers comprise a volatile substance (e.g., a scented material) or a component carrying a volatile substance (e.g., a scented material) that is positioned in a manner that allows accidental contact between a user's hand and the volatile substance and/or the component carrying the volatile substance.

BRIEF SUMMARY OF EXAMPLE EMBODIMENTS

Example embodiments provide a volatile substance diffuser, such as a hollow volatile substance diffuser. In various embodiments, the volatile substance diffuser is a scent diffuser. In various embodiments, a volatile substance diffuser is configured to be removably secured to an automobile vent (e.g., clipped onto a slat of the automobile air vent). In various embodiments, the volatile substance diffuser comprises a component carrying a volatile substance (e.g., scent material) that is disposed within a housing of the volatile substance diffuser in a manner that greatly reduces the chances of a user's hand accidently coming in contact with the component carrying the volatile substance.

According to one aspect, a hollow volatile substance diffuser is provided. In an example embodiment, the hollow volatile substance diffuser comprises a housing defining a housing axis; and a component carrying a volatile substance (e.g., scent material). The component defines an air passageway there through. The component is secured to an inner surface of the housing. The air passageway defines an air passageway axis and the housing axis and the air passageway axis are approximately parallel.

According to another aspect, a hollow volatile substance diffuser is provided. In an example embodiment, the hollow volatile substance diffuser comprises a housing comprising a cylindrical shell; and a cylindrical ring. The cylindrical ring is disposed on an inner surface of the cylindrical shell of the housing. The cylindrical ring comprises and/or carries volatile substance.

BRIEF DESCRIPTION OF THE SEVERAL VIEWS OF THE DRAWING(S)

Having thus described some example embodiments in general terms, reference will now be made to the accompanying drawings, which are not necessarily drawn to scale, and wherein:

DETAILED DESCRIPTION OF SOME EXAMPLE EMBODIMENTS

Various embodiments now will be described more fully hereinafter with reference to the accompanying drawings, in which some, but not all embodiments are shown. Indeed, certain embodiments may be embodied in many different forms and should not be construed as limited to the embodiments set forth herein; rather, these embodiments are provided so that this disclosure will satisfy applicable legal requirements. The term "or" (also denoted "/") is used herein in both the alternative and conjunctive sense, unless otherwise indicated. The terms "illustrative" and "exemplary" are used to be examples with no indication of quality level. The terms "generally" and "approximately" refer to within the appropriate engineering and/or manufacturing tolerances, unless otherwise indicated. Like numbers refer to like elements throughout.

Figure 1:
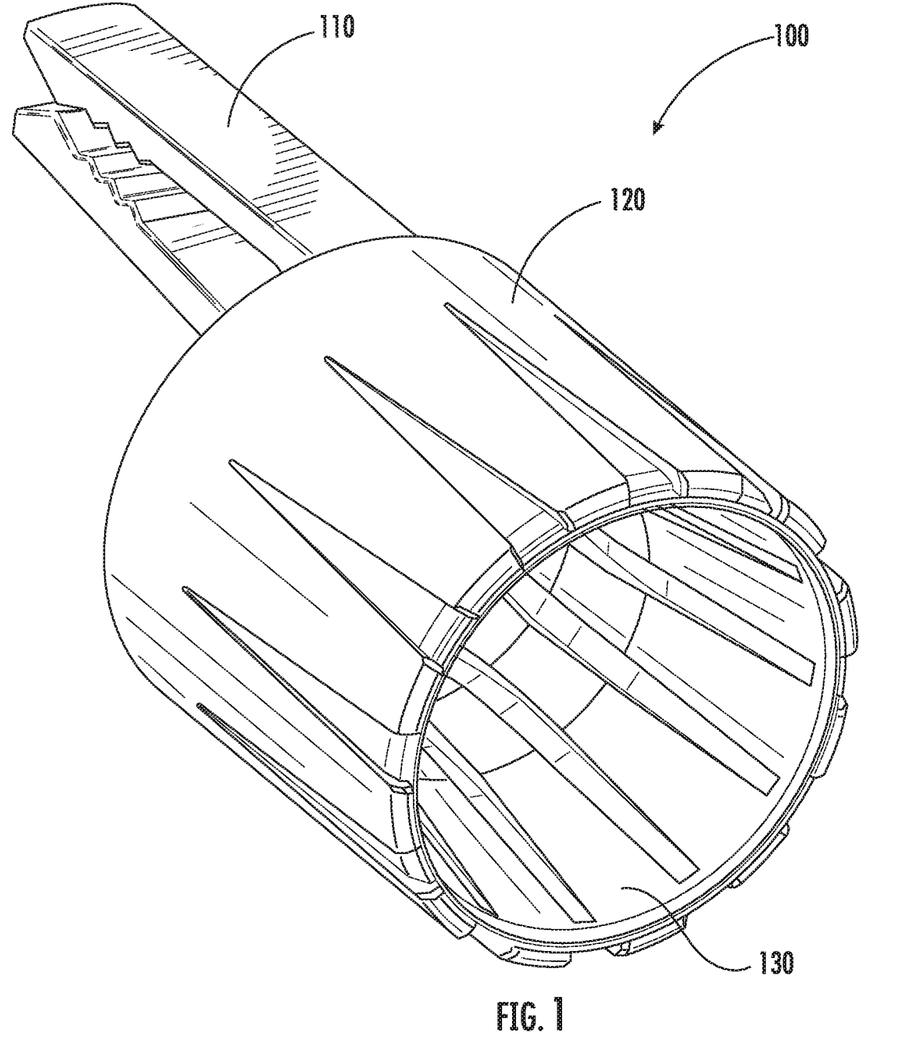
FIG. 1 provides a front top perspective view of a hollow volatile substance diffuser in accordance with an example embodiment.
Figure 2:
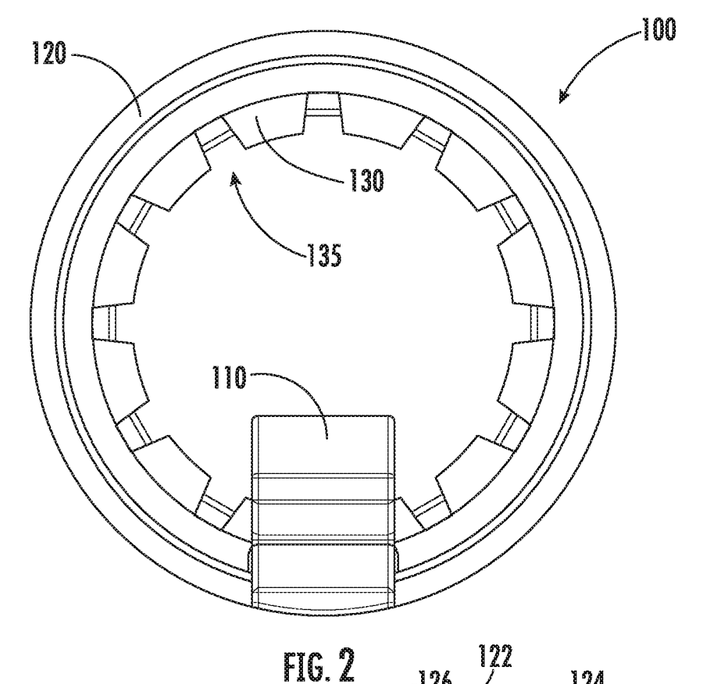
FIG. 2 provides a back view of the hollow volatile substance diffuser illustrated in FIG. 1.
Figure 3:
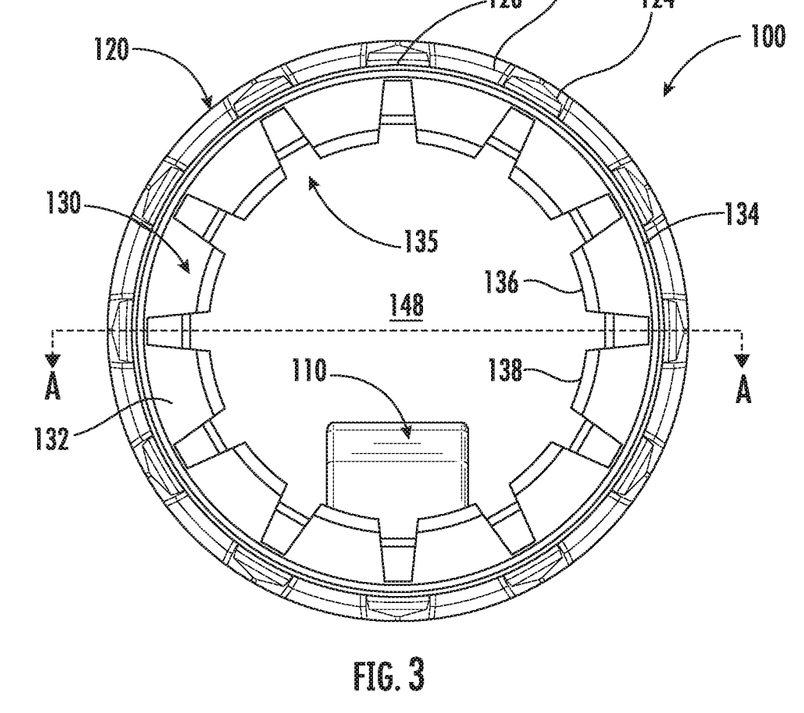
FIG. 3 provides a front view of the hollow volatile substance diffuser illustrated in FIG. 1.
Figure 4:
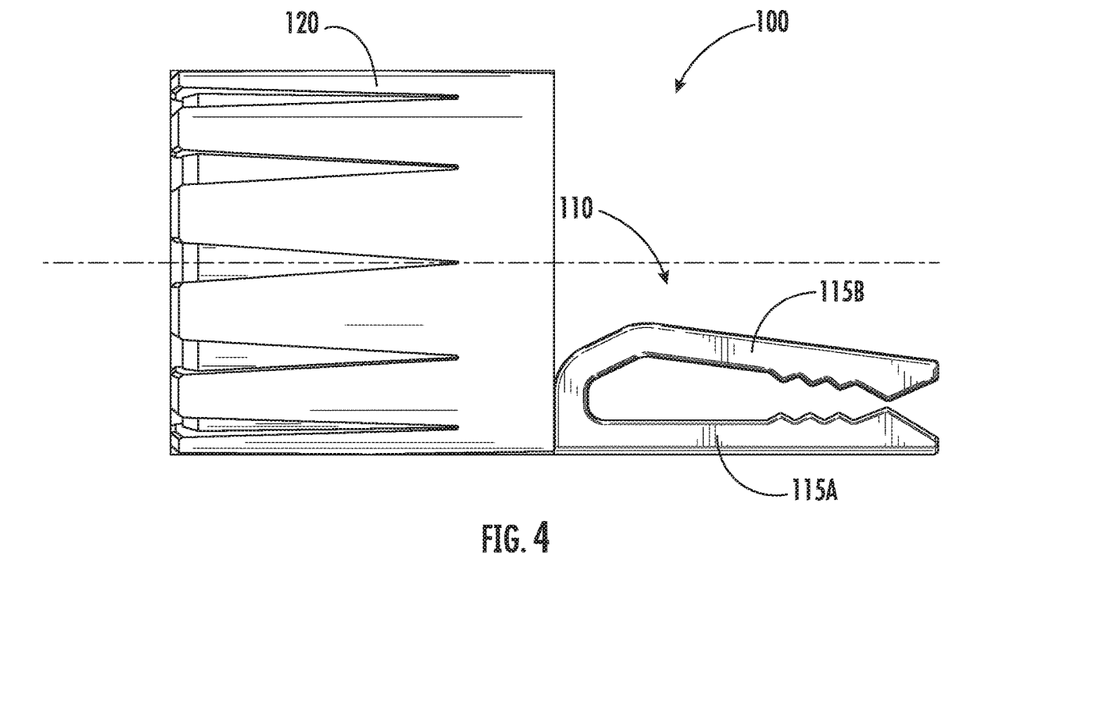
FIG. 4 provides a side view of the hollow volatile substance diffuser illustrated in FIG. 1.
Figure 5:
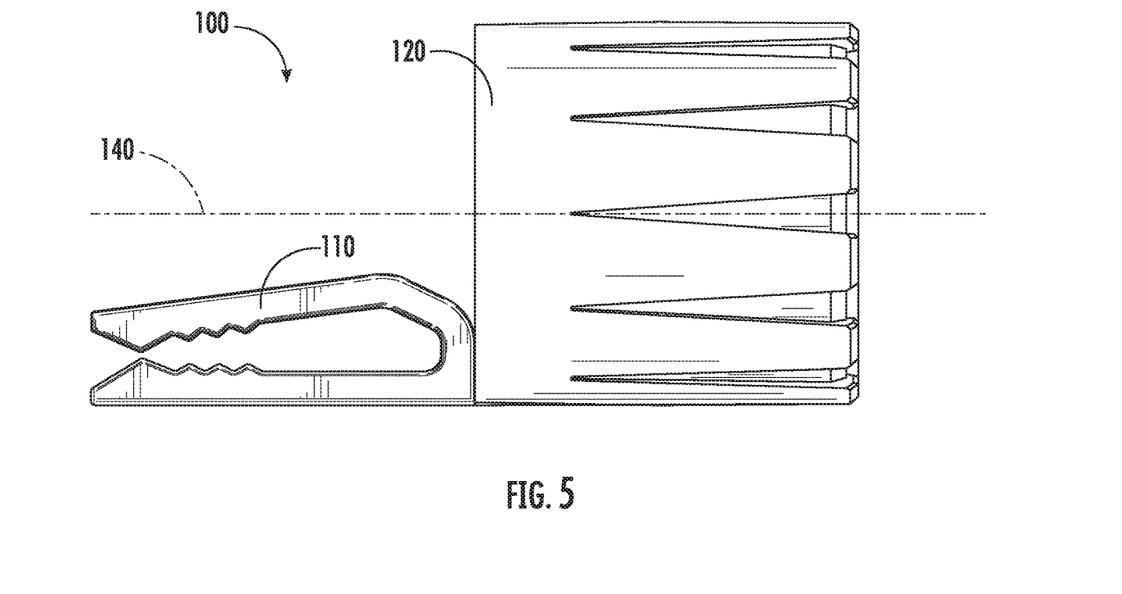
FIG. 5 provides an opposite side view of the hollow volatile substance diffuser illustrated in FIG. 1.
Figure 6:
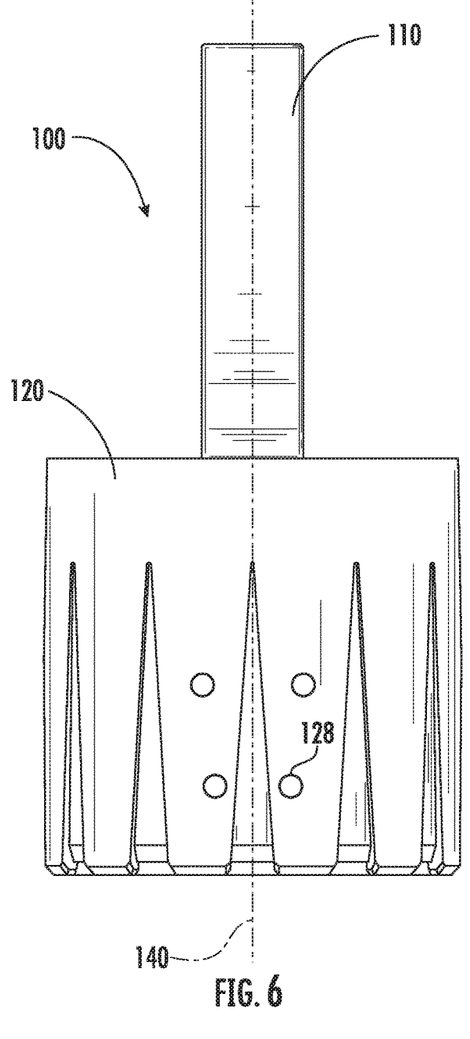
FIG. 6 provides a top view of an example embodiment of a hollow volatile substance diffuser.
Figure 7:
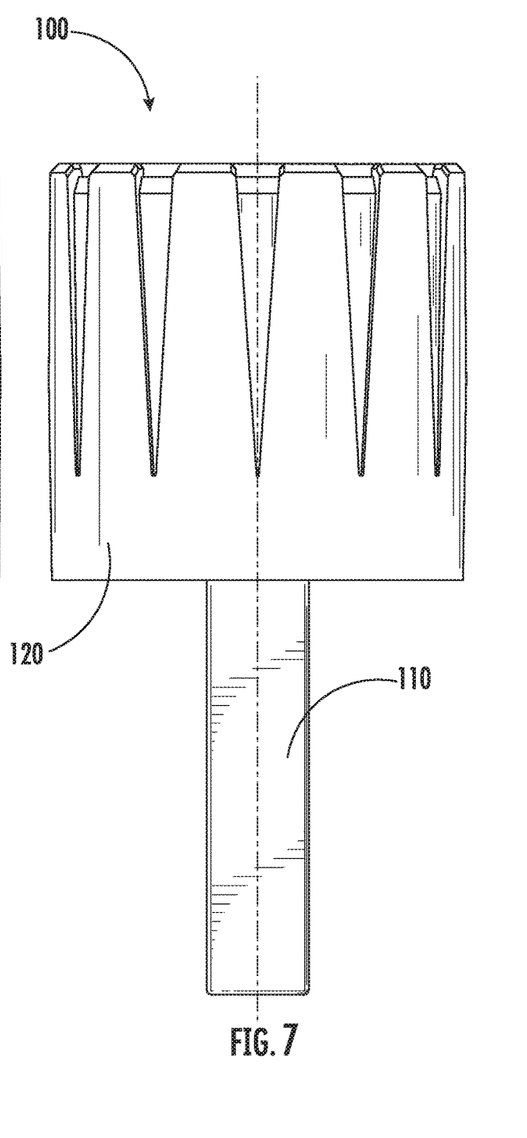
FIG. 7 provides a bottom view of the hollow volatile substance diffuser illustrated in FIG. 1.
Figure 8:
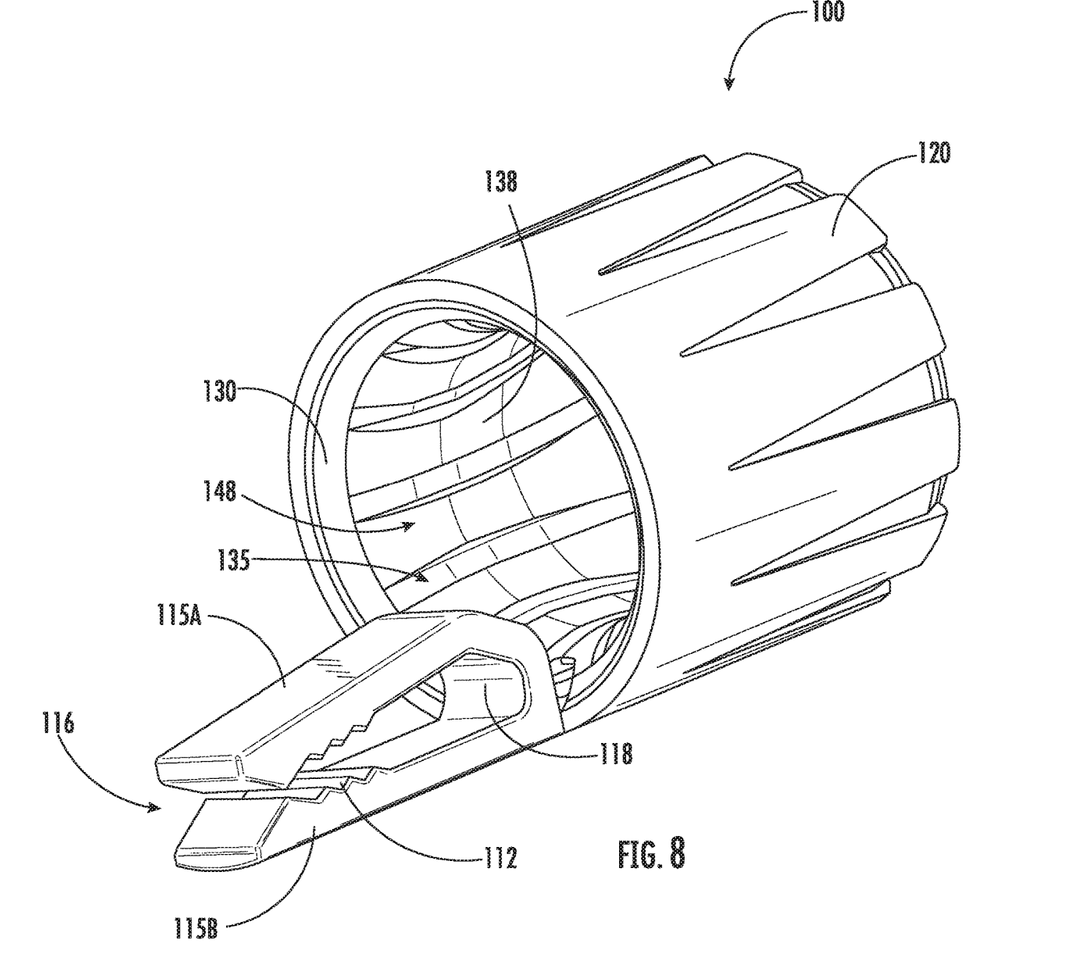
FIG. 8 provides a bottom back perspective view of the hollow volatile substance diffuser illustrated in FIG. 1.
Figure 9:
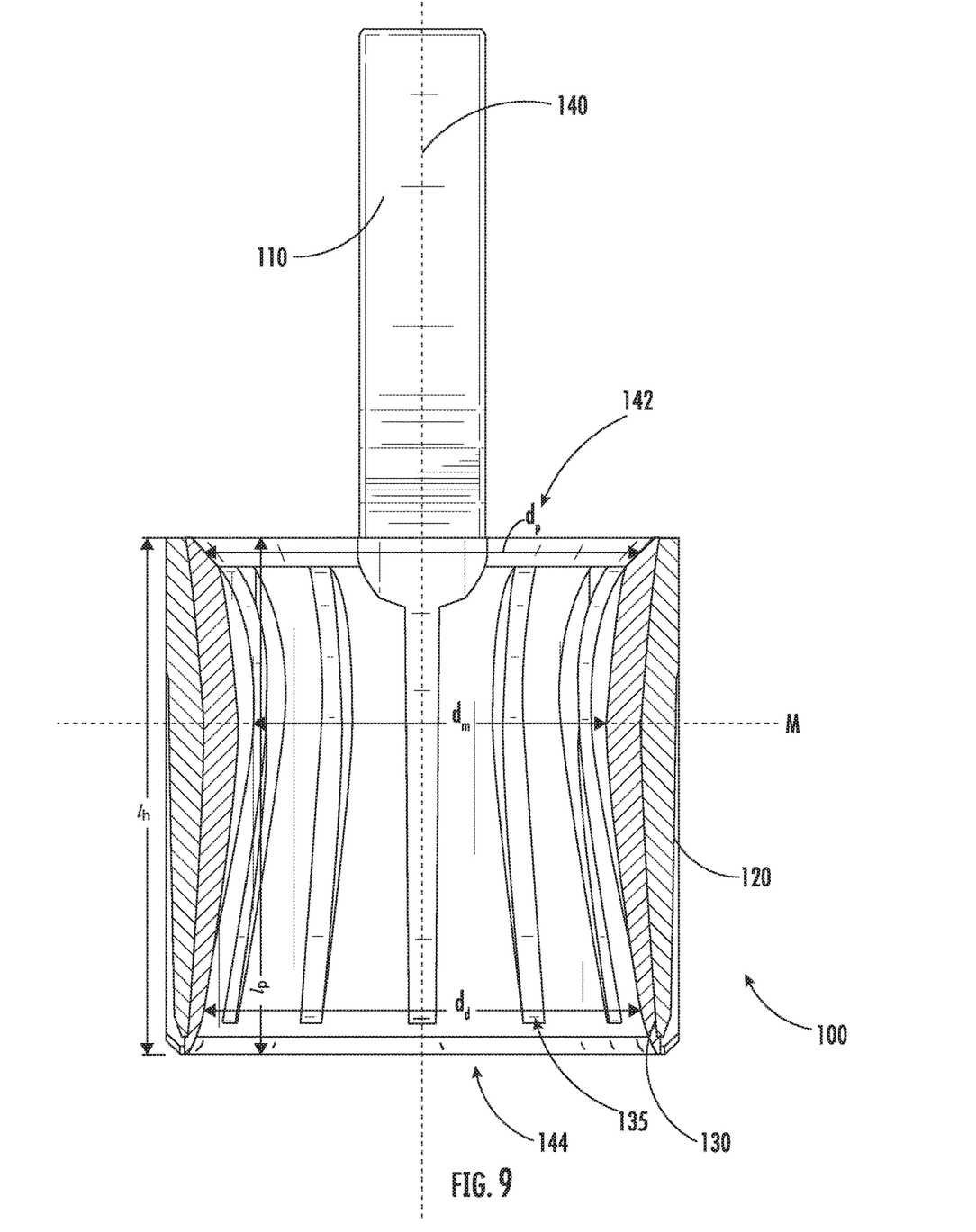
FIG. 9 provides a cross-sectional view of the hollow volatile substance diffuser illustrated in FIG. 1, with the cross-section taken at line A-A in FIG. 3.

FIGS. 1-9 provide various views of an example embodiment of a volatile substance diffuser 100. In various embodiments, the volatile substance diffuser 100 comprises a housing 120 and a clip 110 that is secured to the housing. In an example embodiment, the clip 110 is configured to removably secure the volatile substance diffuser 100 to a slat of an automobile air vent or other air vent (e.g., a building air vent, and/or the like). In various embodiments, the volatile substance diffuser 100 further comprises a component 130 configured to carry a volatile substance.

It should be understood that any of a variety of volatile substances may be utilized with the volatile substance diffuser 100. For example, fragrance compositions (fragrant organic compounds, fragrant volatile oils, fragrant synthetic compounds, and/or the like), deodorizers, disinfectant compositions, medicinal compositions, aroma therapy compositions, insecticides, odor neutralizing composition, and/or the like may be dispersed via the volatile substance diffuser 100. The terms fragrance, scent, and odor are used interchangeably herein. In certain embodiments, the volatile substance diffuser 100 may be embodied as a fragrance diffuser (also known as an air freshener), however other configurations may be possible in accordance with various embodiments discussed herein. Moreover, as discussed herein, the volatile substance may be embedded or otherwise infused within a component 130 (such as a polymer or other material) such that the volatile substance may slowly evaporate and/or sublimate from the component 130 into a flow of air passing over/around the component 130.

In various embodiments, the housing 120 of the volatile substance diffuser 100 comprises and/or forms a cylindrical shell 122 having a hollow interior and open ends. In various embodiments, the cross-sectional shape of the cylindrical shell 122 in a cross-section taken perpendicular to the cylinder axis 140 of the cylindrical shell is circular, oval, rectangular, polygonal, irregular, and/or the like. In various embodiments, the housing 120 is a molded or etched polymeric material, such as styrene-butadiene-styrene (SBS), high-density polyethylene (HDPE), and/or the like. In certain embodiments, the housing 120 may have a coating (e.g., paint, a colorant, a polymer-based sealant, and/or the like) to provide desirable aesthetic and functional characteristics to the housing 120. For example, the housing 120 may have a chrome appearance in certain embodiments. Moreover, it should be understood that other materials may be utilized for formation of the housing, materials such as metal (e.g., aluminum), carbon fiber, or other materials may be utilized in certain embodiments.

In various embodiments, the cylindrical shell 122 comprises a proximal end 142 and a distal end 144. In an example embodiment, a clip 110 is secured to the proximal end 142 of the cylindrical shell. In embodiments, clip 110 may be any attachment mechanism that allows the diffuser 100 to function as described herein, such as a magnetic-based attachment mechanism, a hook-and-loop fastener based attachment mechanism, a clamp attachment mechanism, a tacky or otherwise adhesive-based attachment mechanism, and/or the like. As discussed herein, the clip 110 or other attachment mechanism may be rigidly secured relative to the cylindrical shell 122 so as to maintain a consistent positioning of the clip 110 or other attachment mechanism relative to the cylindrical shell 122. In other embodiments, the clip 110 or other attachment mechanism may be pivotably, rotatably, slidably, or otherwise movably secured relative to the cylindrical shell 122 to enable a user to position the clip 110 or other attachment mechanism relatively to the cylindrical shell 122 (e.g., to accommodate different shaped/configured air vent slats, to redirect the flow of air with absorbed volatile substance, and/or the like). For example, the volatile substance diffuser 100 may be configured to be removably secured to a slat of an air vent such that the proximal end 142 of the cylindrical shell 122 is adjacent to the air vent and the distal end 144 of the cylindrical shell 122 is separated from the air vent by the housing length $\ell_h$. In an example embodiment, the housing length $\ell_h$ is the length or height of the cylindrical shell 122. For example, the housing length $\ell_h$ may be measured in a direction that is parallel to the housing axis, which is coaxial with the cylinder axis 140 defined by the cylindrical shell 122, in the illustrated embodiment. In various embodiments, the housing 120 of the volatile substance diffuser 100 comprises an exterior surface 124 and an inner surface 126. In an example embodiment, the exterior surface 124 forms at least a portion of the exterior surface of the housing 120. In an example embodiment, the cylindrical shell 122 is thin relative to the diameter of the cylindrical shell and relative to the housing length $\ell_h$. For example, the distance between the exterior surface 124 and the inner surface 126 is less than the diameter of the cylindrical shell and relative to the housing length $\ell_h$. In various embodiments, the distance between the exterior surface 124 and the inner surface 126 is less than or approximately half an inch, a quarter of an inch, an eighth of an inch, a tenth of an inch, a sixteenth of an inch, a centimeter, half a centimeter, a quarter of centimeter, ten millimeters, five millimeters, and/or the like.

In an example embodiment, the housing length $\ell_h$ is approximately equal to or greater than half an inch, one inch, an inch and a half, two inches, one centimeter, two centimeters, five centimeters, and/or the like. In an example embodiment, the housing length $\ell_h$ is approximately equal to or less than four inches or ten centimeters. In an example embodiment, the diameter of the cylindrical shell 122 (e.g., the distance between opposite points on the exterior surface 124 in a cross-section taken perpendicular to the cylinder axis 140) is approximately equal to or greater than half an inch, one inch, an inch and a half, two inches, one centimeter, two centimeters, or five centimeters. In an example embodiment, the diameter of the cylindrical shell 122 is approximately equal to or less than three inches or eight centimeters.

In various embodiments, the volatile substance diffuser 100 comprises a component 130 configured to carry a volatile substance. As used herein, volatile can mean evaporative diffusion or other particles that disperse or diffuse to ambient air. In an example embodiment, the volatile substance is an odor absorbing material (e.g., activated charcoal and/or the like). In an example embodiment, the volatile substance is a fragrance emitting material (e.g., scented oil, a polymer plastic that holds scented oil, paper pulp that holds scented oil, firm gel that holds scented oil, and/or the like). In an example embodiment, the volatile substance comprises a combination of odor absorbing material (e.g. disposed closer to the proximal end 142) and fragrance emitting material (e.g., disposed closer to the distal end 144). In an example embodiment, the component 130 comprises a polymer impregnated with and/or carrying volatile substance. In an example embodiment, the component 130 comprises a fibrous plant material and/or other material impregnated with and/or carrying a volatile substance. In various embodiments, the polymer or other material impregnated with and/or carrying volatile substance is formed into a cylindrical ring 132. In an example embodiment, the cylindrical ring 132 is disposed, secured, and/or adhered to the inner surface 126 of the cylindrical shell 122, within the hollow interior of the cylindrical shell 122. For example, the cylindrical ring 132 may comprise an outer surface 134 and an interior surface 136 and the outer surface 134 may be secured and/or adhered to the inner surface 126 of the cylindrical shell 122 of the housing 120.

In various embodiments, a cross-sectional shape of the cylindrical ring 132 in a cross-section taken perpendicular to the cylinder axis 140 of the cylindrical shell 122 is circular, oval, rectangular, polygonal, irregular, and/or the like. In an example embodiment, the cross-sectional shape of the cylindrical ring 132 is the same as the cross-sectional shape of the cylindrical shell 122 in a cross-section taken perpendicular to the cylinder axis 140. In another example embodiment, the cross-sectional shape of the cylindrical ring 132 is different from the cross-sectional shape of the cylindrical shell 122 in a cross-section taken perpendicular to the cylinder axis 140 (e.g., the cross-sectional shape of the cylindrical shell 122 may be round and the cross-sectional shape of the cylindrical ring 132 is octagonal, in an example embodiment).

In various embodiments, the polymer comprising the component 130 carrying the volatile substance may be flexible and resilient, such as a polymer gel (e.g., a non-flowable gel), and may be substantially opaque, translucent or combinations thereof. The polymer may be elastic and coherent. Thus, the polymer body may be compressible under an applied force, and substantially returnable to an original configuration upon removal of the applied force. In an example embodiment, the volatile substance is a scent material or neutralizing agent that may disperse or diffuse out of the component 130 and/or cylindrical shell 132 into the air or atmosphere where it can be detected, or where it can provide a discernable scent, or can neutralize odors. The volatile substance can be high in volatile notes, or have high volatility and can vaporize or evaporate at low temperatures. The volatile substance can include a scented oil. For example, suitable scented oil can include pine, berry, vanilla, apple, coconut, cherry, pina colada, or other scents.

In various embodiments, the polymer of the component 130 carrying volatile substance (e.g., the cylindrical ring 132) may comprise a polymeric material in the glass state with substantially no macroscopic flow. The polymeric material can have a glass transition temperature greater than approximately 110° F. The polymer can retain its gel-like characteristic over time, without drying or cracking, and without becoming hard or brittle. In various embodiments, the polymer of the component 130 carrying volatile substance (e.g., the cylindrical ring 132) may comprise a scented oil and a polymerizable monomer can be combined, along with optional initiators or other reactants. For example, the polymerizable monomer may comprise isocyanate reaction polymers. For example, the polymer gel and scent material can be a urethane polymerization product of combining a scented oil or other volatile substance with a polyether polyol, and then with a diphenylmethane diisocyanate (MDI) prepolymer. Therefore, in some embodiments, the volatile substance can be a scented oil which participates in the polymerization reaction between polymerization reactants. For example, essential oils such as terpenes and the like can be mixed with polymerization reactants, or even in place of some reactants. Other suitable isocyanates can include, but are not limited to, tolylene diisocyanates, methylene diphenyl isocyanates, hexamethylene diisocyanates, prepolymers thereof, and the like. Those skilled in the art will recognize various other isocyanate reaction polymers, i.e. polyurethanes, which can be suitable for use in connection with various embodiments. Alternatively, in an example embodiment of the component 130 carrying volatile substance (e.g., the cylindrical ring 132) may include silicone, diffused polyurethane, polyvinylchloride (PVC), ethylene vinyl acetate (EVA), thermoplastic polyurethane (TPU), a polymer encapsulation fragrance delivery platform (PolyIFF®), thermoplastic elastomer (TPE), polypropylene, ethylene/methacrylic acid (E/MAA) copolymer, in which the MAA groups have been partially neutralized with lithium ions (Surlyn® Dupont), etc. In various embodiments, the polymer of an example embodiment of the component 130 carrying volatile substance (e.g., the cylindrical ring 132) can be formed of an elastomer such as, but not limited to, urethanes (including polyester and polyether polyol/isocyanate polymerization products), polyacrylates, polybutadienes, ethylene propylene elastomers, silicones, natural and synthetic rubbers, styrene/butadiene block copolymers, and the like. In some embodiments, the polymer of an example embodiment of the component 130 carrying volatile substance (e.g., the cylindrical ring 132) can be formed of a thermoplastic elastomer. Thermoplastic elastomers can be block copolymers such as polyurethanes, polyamides, copolyesters, and styrene-butadiene-styrene polymers. Other thermoplastic elastomers can be elastomer/thermoplastic blends such as ethylene-propylene-diene monomer in an isotactic polypropylene phase or nitrile rubber dispersed in a PVC phase. As used herein, "thermoplastic elastomer" refers to an elastomer which can be heated and processed like thermoplastic materials. Specifically, a thermoplastic elastomer can be heated to a melted or flowable state and then cooled, resulting in reformation of cross-linking and subsequent coherency without a substantial change in mechanical properties such as strength, flexural modulus, elastic modulus, etc.

In various embodiments, the component 130 carrying the volatile substance is hollow such that the component 130 defines an air passageway there through. For example, the cylindrical ring 132 may be hollow. For example, the cylindrical ring 132 may define an air passageway 148 that enables an air flow to flow through the component 130 carrying the volatile substance. For example, cylindrical ring 132 may be configured to enable flow of air through the cylindrical ring 132 from the proximal end 142 of the housing 120 through the distal end 144 of the housing 120. In some embodiments, housing 120 may also include one or more small holes or pores 128 aligned in a substantially radial direction of the housing 120 to allow the volatile substance to emit a scent therethrough. As the air flows through the air passageway 148, the air may interact with the volatile substance impregnated within and/or carried by the cylindrical ring 132 to disperse a scent emitted by the volatile substance into the air flow, to enable a scent carried by the air flow to be absorbed into the volatile substance, and/or the like. In an example embodiment, the air passageway 148 defines an air passageway axis. In an example embodiment, the air passageway axis is parallel to the housing axis and/or the ring axis. In the illustrated embodiment, the air passageway axis is coaxial with the cylinder axis 140.

In an example embodiment, the cylindrical ring 132 is disposed within the housing 120 such that the likelihood of a user accidentally touch the component 130 carrying the volatile substance is low. In an example embodiment, the ring length $\ell_p$ is the length or height of the cylindrical ring 132 measured is a direction parallel to a ring axis defined by the cylindrical ring 132. In various embodiments, the ring length $\ell_p$ is approximately equal to or less than the housing length $\ell_h$. In the illustrated embodiment, the ring axis is coaxial with the cylinder axis 140. In various embodiments, the ring axis and the housing axis are parallel.

In various embodiments, the interior surface 136 of the cylindrical ring 132 is smooth or textured. For example, the interior surface 136 of the cylindrical ring may be textured to increase the surface area of the cylindrical ring 132 available to interact with an air flow flowing through the cylindrical ring 132. In an example embodiment, the interior surface 136 of the cylindrical ring 132 comprises a series of valleys 135. For example, the valleys 135 may be separated by corresponding ridges 138. For example, the valleys 135 may be open areas where the distance between the outer surface 134 and the interior surface 136 of the cylindrical ring 132 is reduced compared to the distance between the outer surface 134 and the interior surface 136 of the cylindrical ring 132 at the ridges 138. For example, the ridges 138 may extend out into the air passageway 148 so as to increase the interaction with air flow (e.g., for example by increased surface area in contact with the air flow) flowing through the cylindrical ring 132 and the volatile substance impregnated within and/or carried by the cylindrical ring 132.

In various embodiments, the interior surface 136 of the cylindrical ring 132 is sloped. For example, the interior surface 136 may define a proximal diameter $d_p$ measured and/or defined at, adjacent, and/or near the proximal end 142 of the housing 120, a distal diameter $d_d$ measured and/or defined at, adjacent and/or near the distal end 144 of the housing 120, and a midpoint diameter $d_m$ at a midpoint located between the proximal end 142 and the distal end 144. In an example embodiment, the midpoint diameter is the diameter of the air passageway 148 (e.g., the distance between one point on the interior surface 136 and an opposite point on the interior surface 136 in a cross-section of the component 130 taken perpendicular to the housing axis) along the midpoint line M. In various embodiments, the midpoint line M may be a quarter of the way between the proximal end 142 and the distal end 144, between a quarter of the way and a half of the way between the proximal end 142 and the distal end 144, half of the way between the proximal end 142 and the distal end 144, between half way and three quarters of the way between the proximal end 142 and the distal end 144, three quarters of the way between the proximal end 142 and the distal end 144, and/or the like. In an example embodiment, the proximal diameter $d_p$, distal diameter $d_d$, and midpoint diameter $d_m$ are each measured between two ridges 138, between two valleys 135, or between a ridge 138 and a valley 135. In various embodiments, the proximal diameter $d_p$ is greater than the midpoint diameter $d_m$. In various embodiments, the distal diameter $d_d$ is greater than the midpoint diameter $d_m$. For example, the interior surface 136 of the cylindrical ring 132 may slope inward from the proximal end 142 in toward the ring axis until reaching a midpoint located at a position between the proximal end 142 and the distal end 144. For example, the inward slop of the interior surface 136 may provide for additional interaction between an air flow flowing through the air passageway 148 from the proximal end 142 through the distal end 144 and the cylindrical ring 132 comprising the volatile substance. For example, the interior surface 136 of the cylindrical ring 132 may slope outward from a midpoint located at a position between the proximal end 142 and the distal end 144 away from the ring axis to the distal end 144 of the cylindrical ring 132. For example, the outward slope of the interior surface 136 of the cylindrical ring 132 may cause the air flow flowing through the air passageway 148 to disperse as the air flow approaches and/or exits the air passageway 148 at the distal end 144 of the housing 120. In an example, embodiment, the proximal diameter $d_p$, distal diameter $d_d$, and midpoint diameter $d_m$ define the diameter and/or width of the air passageway 148 at, adjacent, and/or near the proximal end 142 of the housing 120, the distal end 144 of the housing 120, and a midpoint located between the proximal end 142 and the distal end 144 of the housing, respectively.

In an example embodiment, wherein the volatile substance comprises both a scent absorbing material and a scent emitting material, the cylindrical ring 132 may be impregnated with and/or carrying the scent absorbing material between the proximal end 142 and the midpoint and the cylindrical ring 132 impregnated with and/or carrying the scent emitting material between the midpoint and the distal end 144.

In an example embodiment, a clip 110 is secured to the housing 120. In an example embodiment, the clip 110 is configured to removably secure the volatile substance diffuser 100 to a slat of an air vent (e.g., automobile air vent, building air vent, and/or the like). In an example embodiment, the clip 110 is secured to the proximal end 144 of the housing 120. For example, the clip 110 may be immovably secured relative to the proximal end 144 of the housing 120 (e.g., by integrally forming the clip 110 with the housing 120, and/or by otherwise securing the clip 110 relative to the housing). In other embodiments however, the clip 110 may be pivotably secured relative to the proximal end 144 of the housing 120 (e.g., via a ball-and-socket connection, via a hinged connection, and/or the like). Moreover, it should be understood that the clip 110 may be slidably secured relative to the proximal end 144 of the housing 120 in certain embodiments (e.g., enabling the clip to slide around the circumference of the housing 120). Other mechanisms for securing the clip 110 relative to the housing may alternatively or additionally be used in accordance with certain embodiments.

In an example embodiment, the clip 110 comprise fingers 115A, 115B. The fingers 115A, 115B define receiving notch 116. The receiving notch 116 is configured to receive a slat of an air vent therein. In the illustrated embodiment, the clip 110 comprises two fingers 115A, 115B. However, in various embodiments, the volatile substance diffuser 100 comprises a variety of number of fingers and/or finger configurations configured to removably secure the volatile substance diffuser 100 to one or more slats of an air vent (e.g., automobile air vent, building air vent, and/or the like).

Figure 10:
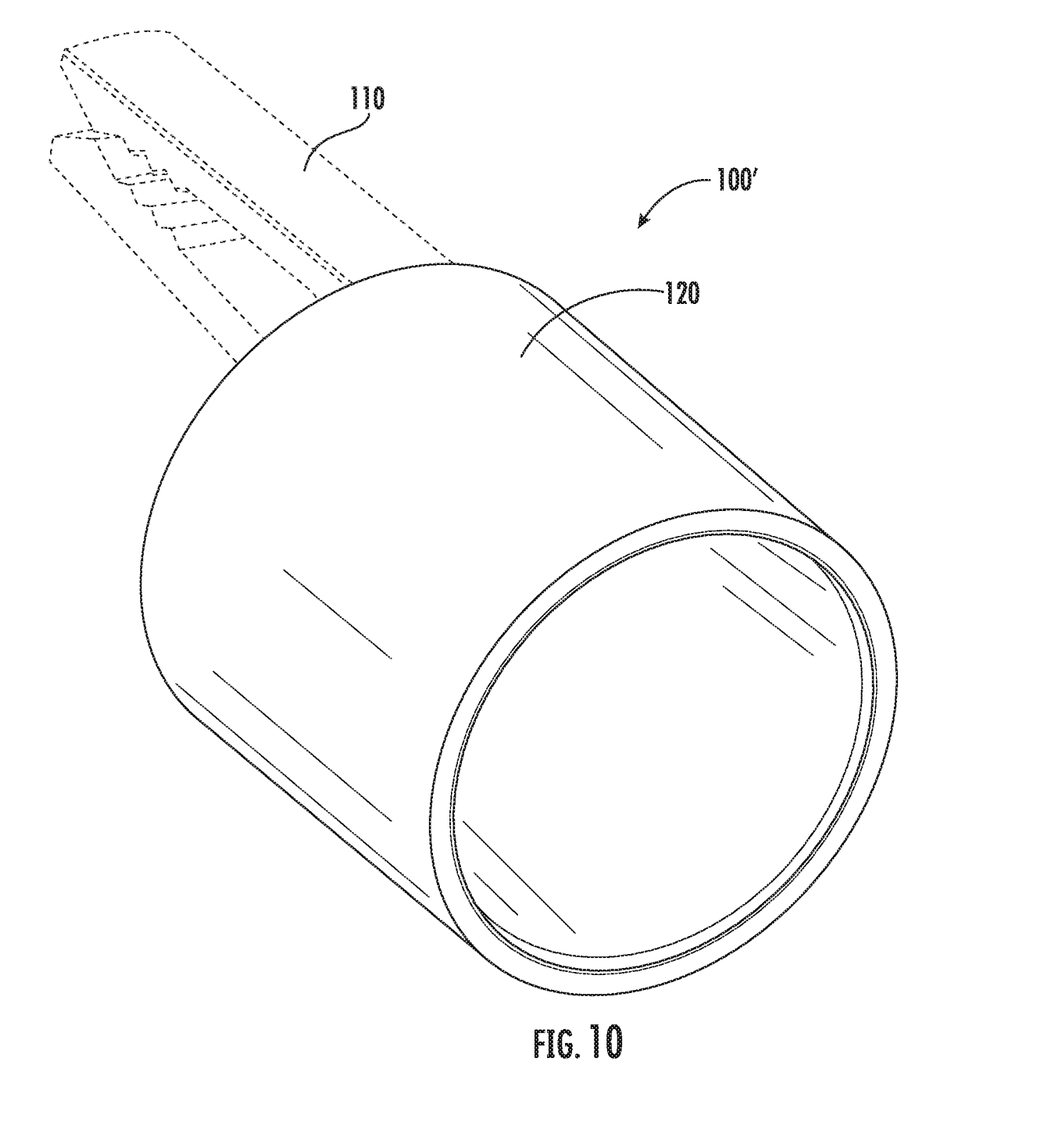
FIG. 10 provides a front top perspective view of a hollow volatile substance diffuser in accordance with another example embodiment.
Figure 11:
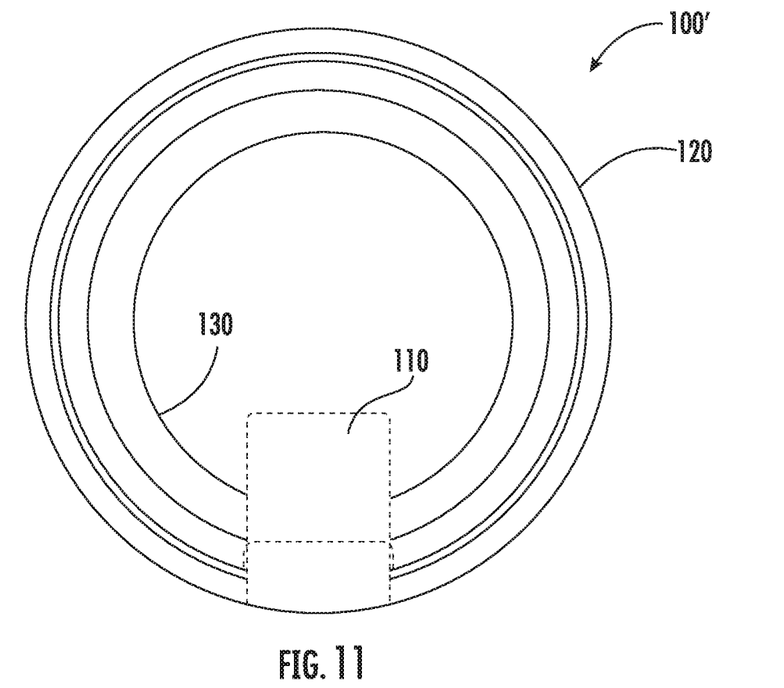
FIG. 11 provides a back view of the hollow volatile substance diffuser illustrated in FIG. 10.
Figure 12:
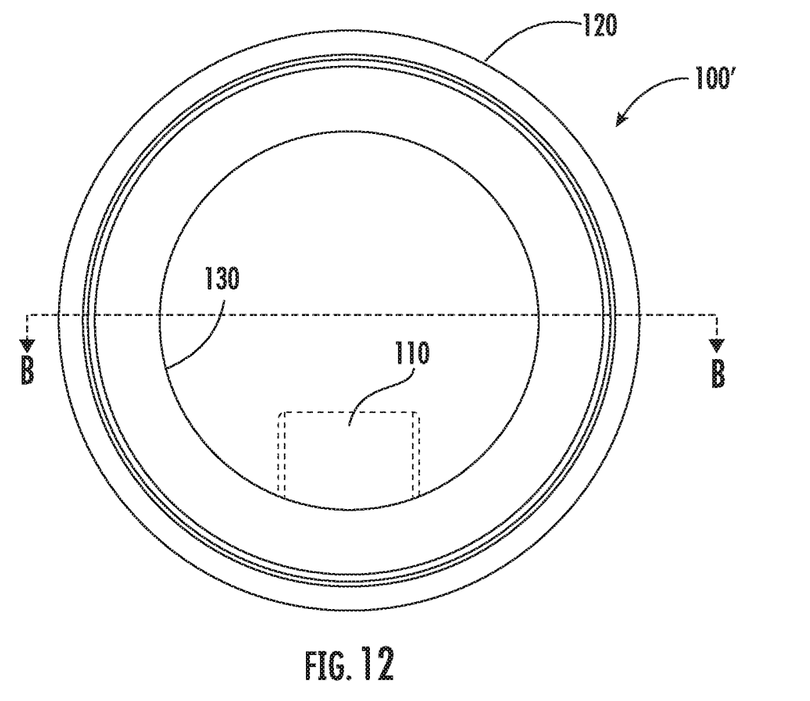
FIG. 12 provides a front view of the hollow volatile substance diffuser illustrated in FIG. 10.
Figure 13:
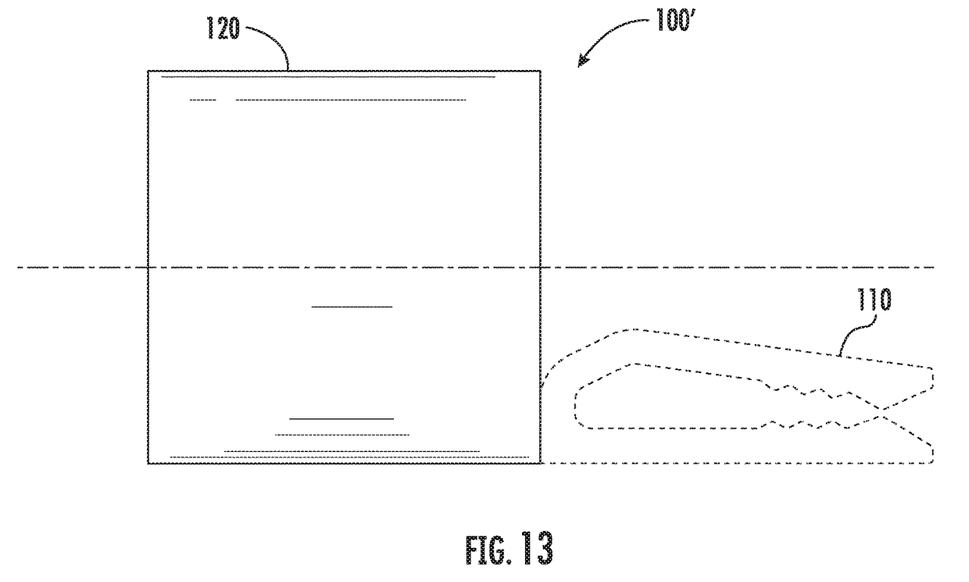
FIG. 13 provides a side view of the hollow volatile substance diffuser illustrated in FIG. 10.
Figure 14:
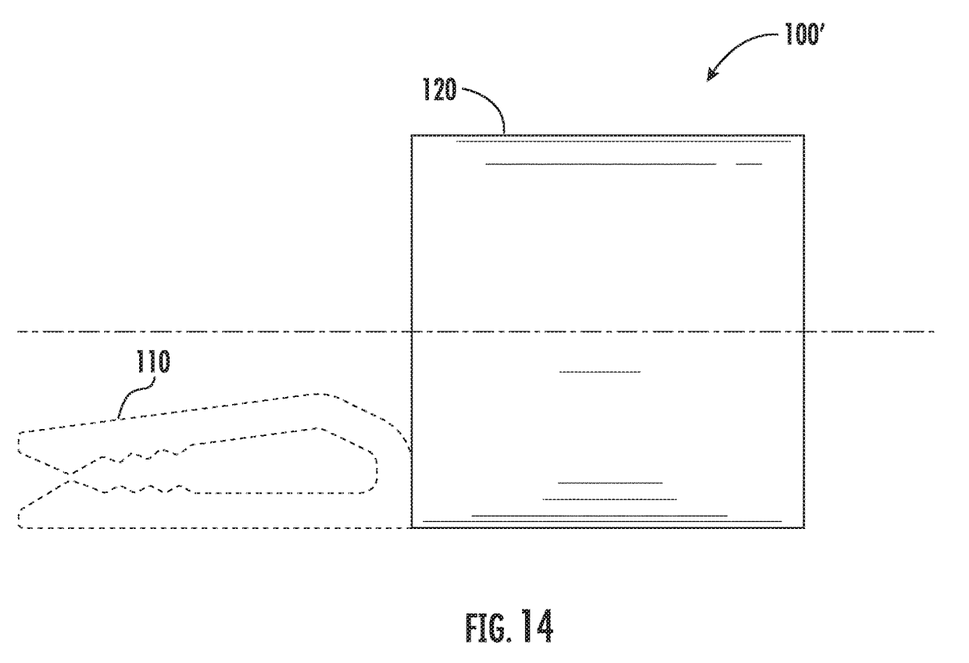
FIG. 14 provides an opposite side view of the hollow volatile substance diffuser illustrated in FIG. 10.
Figure 15:
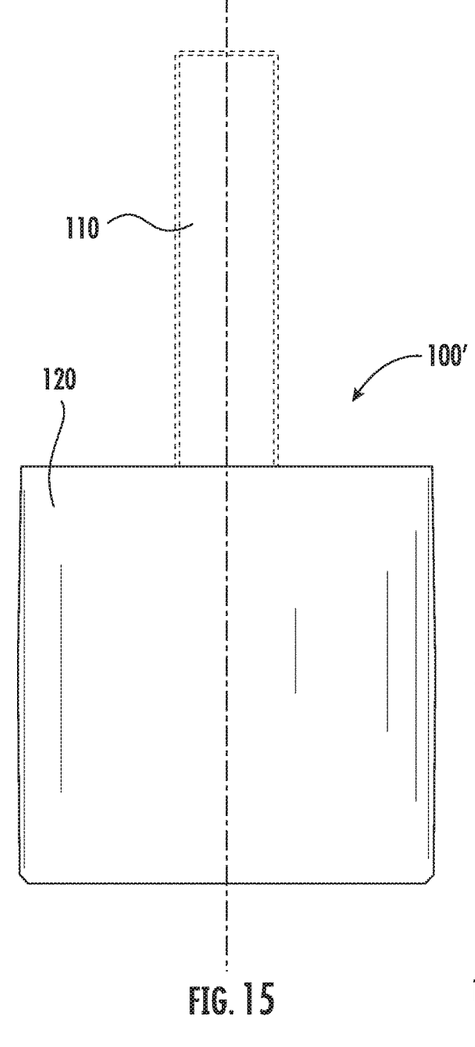
FIG. 15 provides a top view of the hollow volatile substance diffuser illustrated in FIG. 10.
Figure 16:
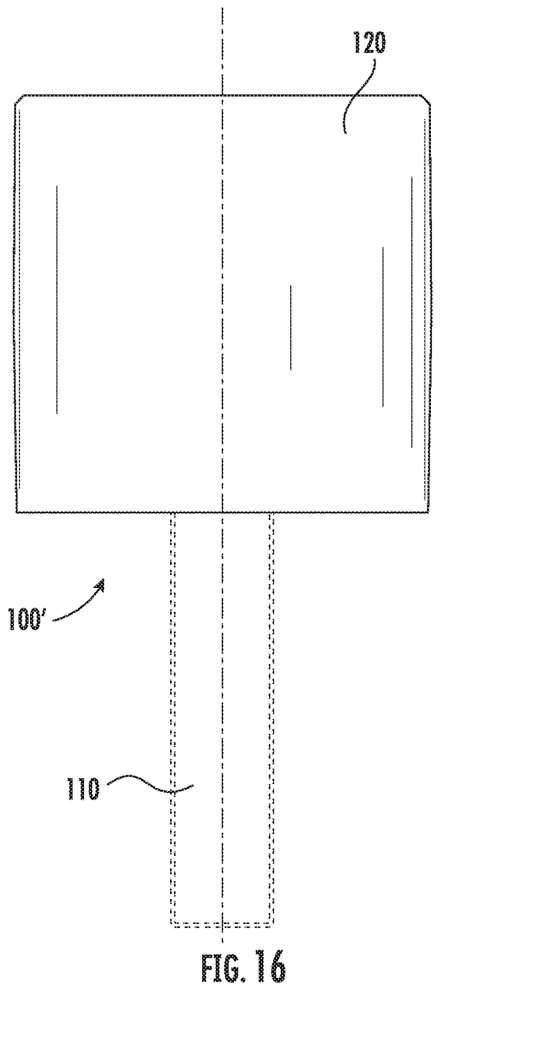
FIG. 16 provides a bottom view of the hollow volatile substance diffuser illustrated in FIG. 10.
Figure 17:
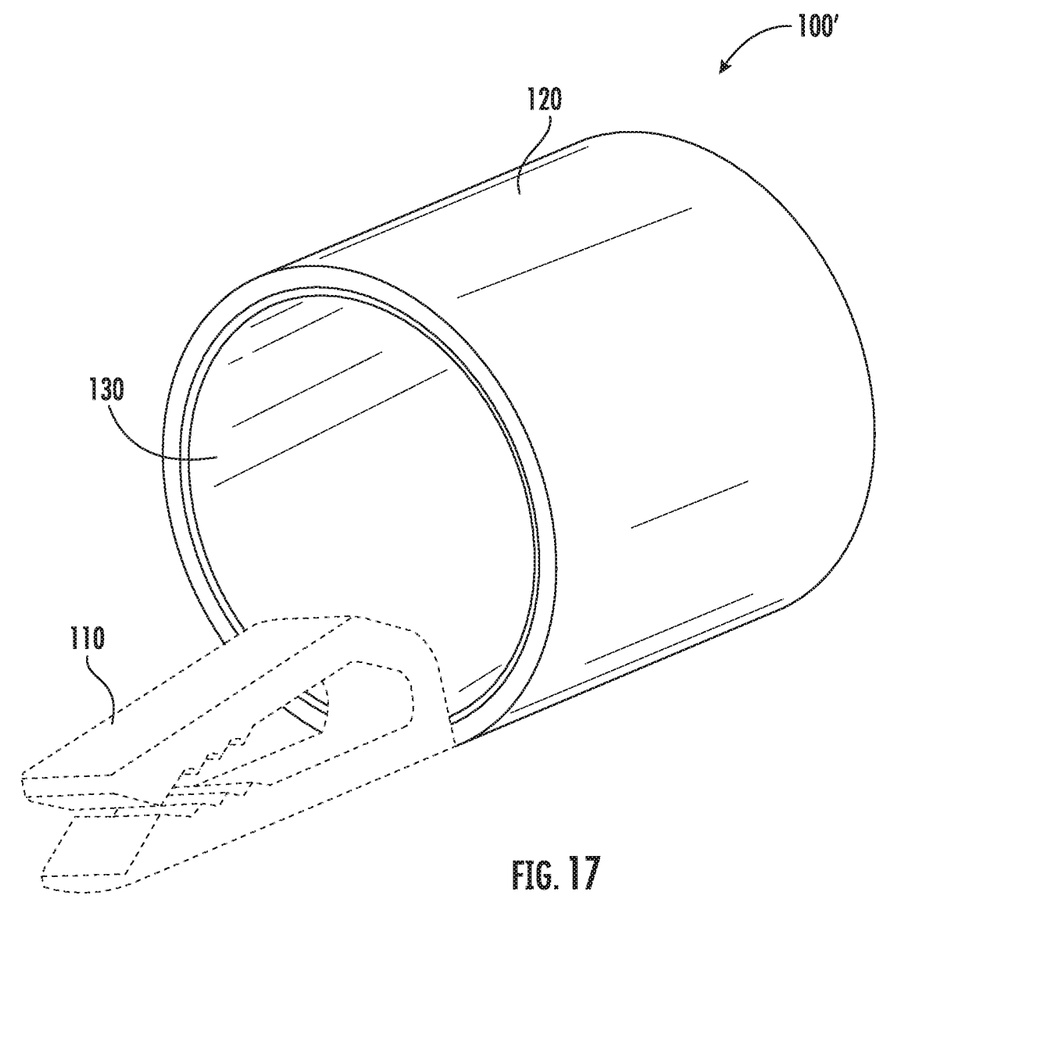
FIG. 17 provides a bottom back perspective view of the hollow volatile substance diffuser illustrated in FIG. 10.
Figure 18:
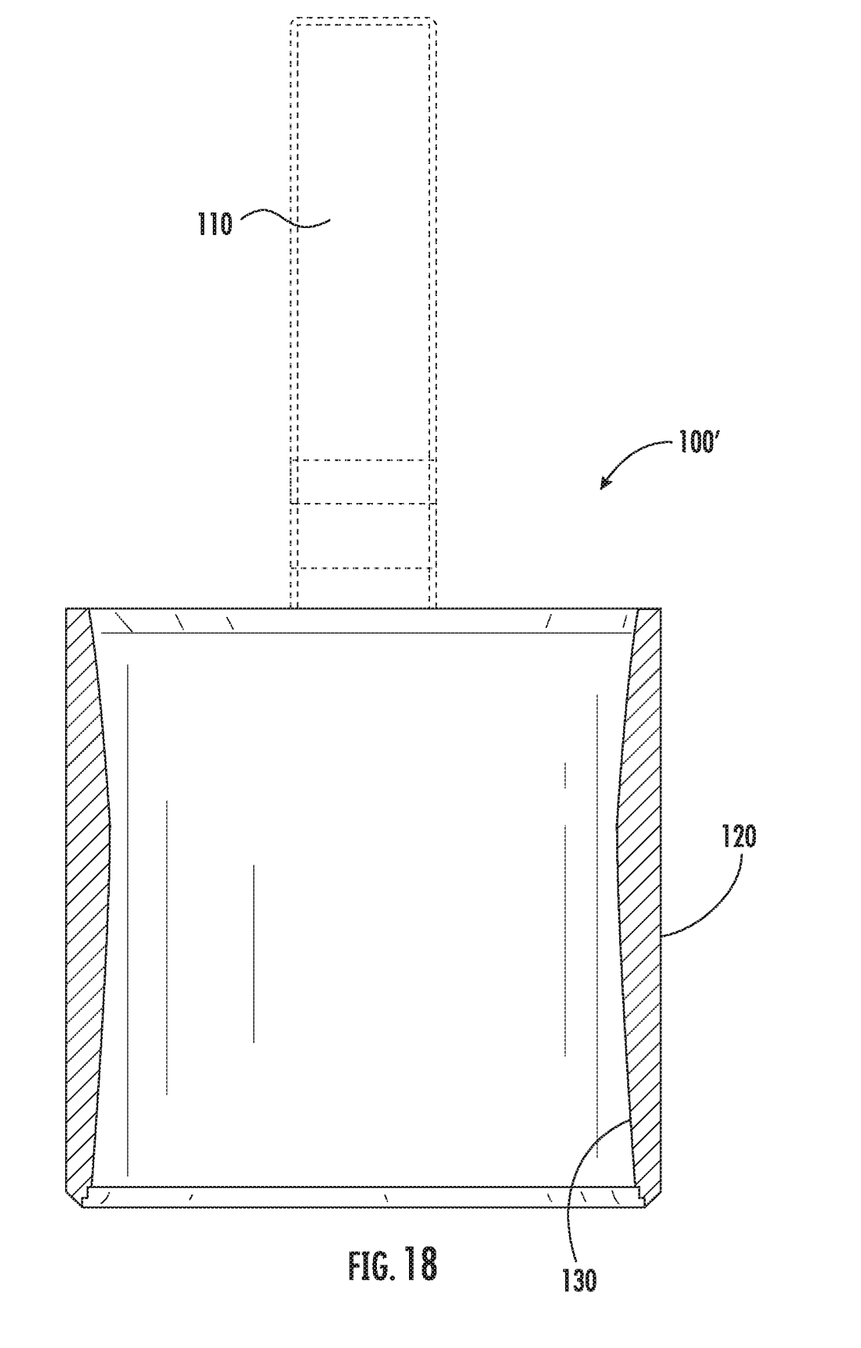
FIG. 18 provides a cross-sectional view of the hollow volatile substance diffuser illustrated in FIG. 10, with the cross-section taken at line B-B in FIG. 12.

In an example embodiment, the exterior surface 124 and/or the interior surface 136 may comprise one or more textures and/or detailing configured to provide a particular aesthetic to the volatile substance diffuser 100. In an example embodiment, the housing 120 and/or the component 130 configured to carry the volatile substance may have a color or plurality of colors configured to provide a particular aesthetic to the volatile substance diffuser 100. In an example embodiment, the housing 120 is black or dark grey, the component 130 is red, and the housing 120 and the component 130 comprise detailing as shown in FIGS. 1-9 so as to provide an aesthetic to the volatile substance diffuser 100 such that the volatile substance diffuser 100 looks like the afterburner of a rocket. Various other aesthetics may be accomplished via various colors of the housing 120 and/or the component 130 configured to carry the volatile substance and various detailing of the housing 120 and/or the component 130. For example, FIGS. 10-17 provide various views of an example embodiment of a volatile substance diffuser 100', wherein the exterior surface 124 and the interior surface 136 are smooth or textured, but do not include detailing.

Many modifications and other embodiments set forth herein will come to mind to one skilled in the art to which the various embodiments pertain having the benefit of the teachings presented in the foregoing descriptions and the associated drawings. Therefore, it is to be understood that the embodiments are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A volatile substance diffuser comprising:
a housing comprising a cylindrical shell having an inner surface and an exterior surface, the housing defining a proximal end having a proximal opening and a distal end having a distal opening; and
a cylindrical ring comprising an outer surface, an interior surface, and a volatile substance, the cylindrical ring being disposed on the inner surface of the cylindrical shell with the outer surface being adjacent to and oriented to face the inner surface of the cylindrical shell, the interior surface defining a hollow air passageway that extends through the proximal opening and distal opening of the housing, the interior surface comprising at least one valley,
wherein the cylindrical ring defines a proximal diameter of the air passageway adjacent the proximal end of the housing and a midpoint diameter of the air passageway at a midpoint along a housing axis defined by the housing between the proximal end and the distal end, and wherein the proximal diameter is different than the midpoint diameter.

2. The volatile substance diffuser of claim 1, further comprising a clip secured to the housing and configured to removably secure the volatile substance diffuser to a slat of an air vent.

3. The volatile substance diffuser of claim 2, wherein the clip is configured to orient the volatile substance diffuser with respect to the air vent such that an airflow through the cylindrical ring is generally along a longitudinal axis of the cylindrical ring.

4. The volatile substance diffuser of claim 1, wherein the volatile substance comprises both an odor absorbing material and a fragrance emitting material.

5. The volatile substance diffuser of claim 1, wherein the cylindrical shell of the housing defines an axial housing length extending from the proximal end of the housing to the distal end of the housing, the cylindrical ring defining an axial ring length, and wherein the axial ring length is approximately equal to the axial housing length.

6. The volatile substance diffuser of claim 1, wherein a ring axis defined by the cylindrical ring is substantially parallel to the housing axis.

7. The volatile substance diffuser of claim 1, wherein the cylindrical shell of the housing and the cylindrical ring are coaxial.

8. The volatile substance diffuser of claim 1, wherein the cylindrical ring is adhered to the inner surface of the cylindrical shell, and wherein the hollow air passageway allows air from outside of the housing to flow into the air passageway through the proximal opening and to exit the housing through the distal opening.

9. The volatile substance diffuser of claim 1, wherein a passageway axis defined by the hollow air passageway is generally parallel to the housing axis, and wherein the cylindrical ring extends from the proximal end of the housing to the distal end of the housing.

10. The volatile substance diffuser of claim 9, wherein the volatile substance diffuser is configured to allow air to flow through the air passageway in an air flow direction that is generally parallel to the passageway axis.

11. The volatile substance diffuser of claim 9, wherein the proximal diameter is larger than the midpoint diameter, and wherein the interior surface extends radially inward from the proximal end of the housing to the midpoint.

12. The volatile substance diffuser of claim 9, wherein the cylindrical ring defines a distal diameter adjacent the distal end of the housing, the distal diameter being larger than the midpoint diameter, and wherein the interior surface extends radially inward from the distal end to the midpoint.

13. The volatile substance diffuser of claim 9, further comprising a clip secured to the proximal end of the housing and configured to removably secure the volatile substance diffuser to a slat of an air vent.

14. The volatile substance diffuser of claim 1, wherein the cylindrical ring is made of a polymer.

15. A volatile substance diffuser comprising:
a housing defining a housing axis, the housing extending axially along the housing axis between a proximal end and a distal end, the proximal end defining a proximal opening and the distal end defining a distal opening, the housing comprising a shell having an inner surface and an exterior surface, the shell defining an axial housing length extending from the proximal end of the housing to the distal end of the housing; and
a component carrying a volatile substance, the component defining an air passageway that allows air to flow through the proximal opening into the housing, through the air passageway, and out of the housing through the distal opening, wherein the component is adhered to the inner surface of the shell, the air passageway defines an air passageway axis, and the housing axis and the air passageway axis are at least substantially parallel, the component defining an axial ring length, wherein the axial ring length is approximately equal to the axial housing length.

16. The volatile substance diffuser of claim 15, further comprising a clip secured to the housing and configured to removably secure the volatile substance diffuser to a slat of an air vent.

17. The volatile substance diffuser of claim 15, wherein the volatile substance comprises at least one of (a) an odor absorbing material or (b) a fragrance emitting material.

18. The volatile substance diffuser of claim 15, wherein the component is hollow.

19. The volatile substance diffuser of claim 15, wherein:
the component defines a proximal diameter adjacent the proximal end of the housing and a midpoint diameter at a point along the housing axis, the proximal diameter is larger than the midpoint diameter, and
the component defines a distal diameter adjacent the distal end of the housing and the distal diameter is larger than the midpoint diameter.

20. The volatile substance diffuser of claim 15, wherein an outer surface of the component is adjacent to the inner surface of the shell, and wherein an interior surface of the component comprises at least one valley.

* * * * *